US006758842B2

(12) United States Patent
Irion et al.

(10) Patent No.: US 6,758,842 B2
(45) Date of Patent: Jul. 6, 2004

(54) MEDICAL INSTRUMENT FOR REMOVING TISSUE, BONE CEMENT OR THE LIKE IN THE HUMAN OR ANIMAL BODY

(75) Inventors: Klaus M. Irion, Liptingen (DE); Nicanor G. Isse, Burbank, CA (US)

(73) Assignee: Karl Storz GmbH & Co. KG (DE)

( * ) Notice: Subject to any disclaimer, the term of this patent is extended or adjusted under 35 U.S.C. 154(b) by 50 days.

(21) Appl. No.: 09/930,897

(22) Filed: Aug. 16, 2001

(65) Prior Publication Data

US 2002/0022854 A1 Feb. 21, 2002

Related U.S. Application Data

(63) Continuation of application No. PCT/EP00/12829, filed on Dec. 15, 2000.

(30) Foreign Application Priority Data

Dec. 16, 1999 (DE) .......................................... 199 61 027

(51) Int. Cl.$^7$ ............................................... A61B 17/22
(52) U.S. Cl. .......................... 604/542; 604/22; 606/171
(58) Field of Search .......................... 604/22, 35, 902, 604/542, 147, 141, 143, 152; 606/171; 222/320

(56) References Cited

U.S. PATENT DOCUMENTS

| | | | |
|---|---|---|---|
| 4,886,491 A | | 12/1989 | Parisi et al. .................. 604/22 |
| 5,019,035 A | * | 5/1991 | Missirlian et al. ............ 604/22 |
| 5,685,840 A | | 11/1997 | Schechter et al. ............ 604/22 |
| 5,795,323 A | * | 8/1998 | Cucin .......................... 604/22 |
| 5,911,700 A | * | 6/1999 | Mozsary et al. .............. 604/22 |
| 6,102,885 A | * | 8/2000 | Bass ............................ 604/22 |
| 6,206,873 B1 | * | 3/2001 | Paolini et al. ................. 606/7 |
| 6,213,971 B1 | * | 4/2001 | Poole ........................... 604/35 |
| 6,296,638 B1 | * | 10/2001 | Davison et al. .............. 606/41 |
| 6,461,350 B1 | * | 10/2002 | Underwood et al. ......... 606/32 |

FOREIGN PATENT DOCUMENTS

| | | |
|---|---|---|
| DE | 34 39 434 | 4/1986 |
| DE | 44 05 656 | 8/1995 |
| DE | 198 17 979 | 11/1999 |
| DE | 199 61 027 | 6/2001 |
| WO | WO99/09897 | 3/1999 |

* cited by examiner

*Primary Examiner*—Michael J. Milano
*Assistant Examiner*—Bradford C Pantuck
(74) *Attorney, Agent, or Firm*—St. Onge Steward Johnston & Reens LLC

(57) ABSTRACT

A medical instrument for treating, in particular for removing tissue, bone cement or the like in the human or animal body, comprising a hand piece having a distal end; an application part arranged at said distal end said hand piece, said application part being axially movable to-and-fro relative to said hand piece; a drive mechanism for said application part, said drive mechanism being provided in said hand piece, said drive mechanism transferring a pressure being continuously present in said hand piece into said to-and-fro movement of said application part, wherein said application part has at least in a region of a distal end of said application part a conduit, which has, in a distal region of said conduit, at least a suction and/or irrigation aperture.

22 Claims, 3 Drawing Sheets

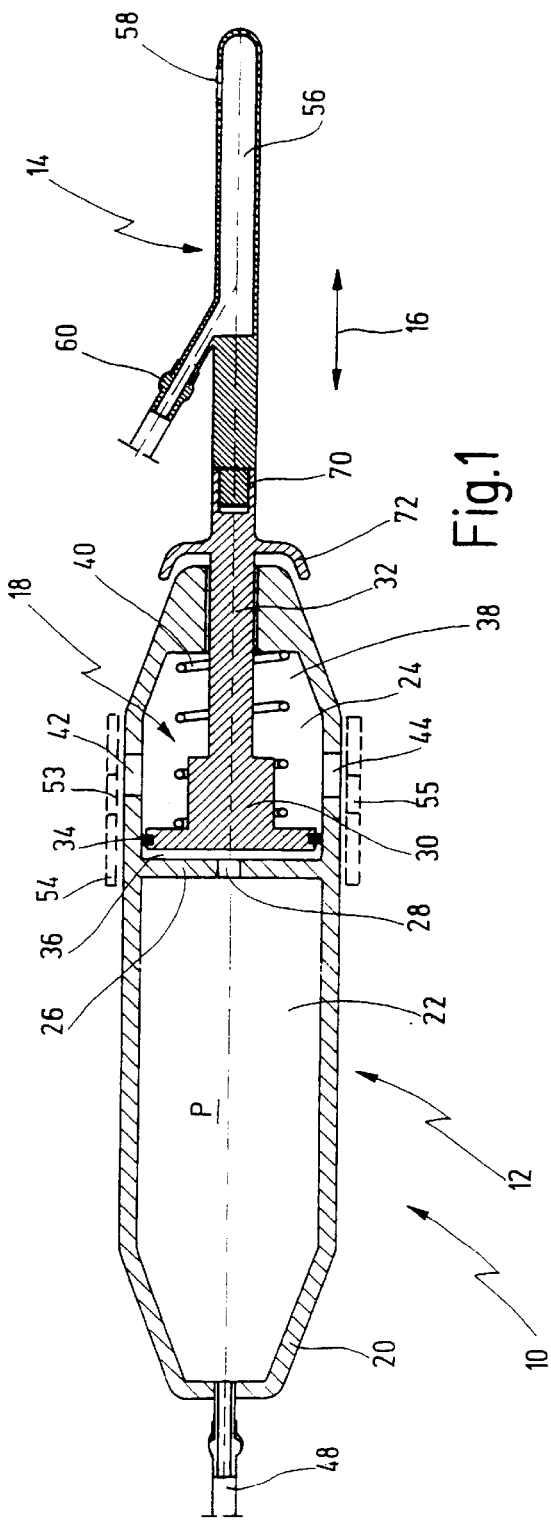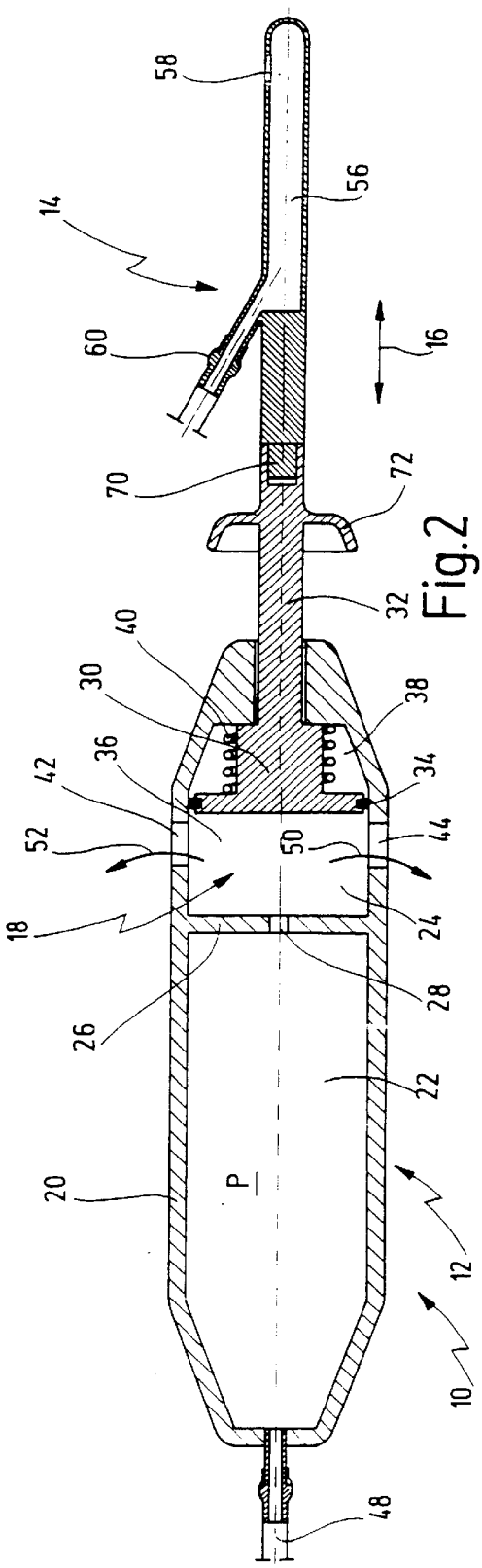

MEDICAL INSTRUMENT FOR REMOVING TISSUE, BONE CEMENT OR THE LIKE IN THE HUMAN OR ANIMAL BODY

CROSS REFERENCE TO PENDING APPLICATION

This application is a continuation of pending International Patent Application PCT/EP00/12829 filed on Dec. 15, 2000, which designates the United States, and which claims priority of German Patent Application 199 61 027 filed on Dec. 16, 1999.

BACKGROUND OF THE INVENTION

The invention relates to a medical instrument for treating, in particular for removing tissue, bone cement or the like in the human or animal body, comprising a hand piece and an application part arranged on the distal end of same, wherein the application part is axially movable to-and-fro relative to the hand piece, wherein the hand piece contains a drive mechanism for the application part, which transfers a pressure being continuously present in the hand piece in the to-and-fro movement of the application part.

Such an instrument is known from DE 34 39 434 A1.

The known instrument mentioned before serves for the creation of mechanical oscillations for medical curing purposes even in deeper body layers.

An instrument mentioned at the outset is to be suitable, according to the present invention to remove biological tissue, in particular soft or fatty tissue, from the human or animal body. A special application of such an instrument is the removal by suction of fat within the scope of cosmetic surgery. Another application of such an instrument is the removal of bone cement, by which an endoprosthesis, e.g. a hip joint endoprosthesis, is anchored in a bone of the human skeleton, in order to be able to take the endoprosthesis out of the bone for the purpose of revision.

From U.S. Pat. No. 5,685,840, an instrument is known that has an application part having an opening at its distal end and a cutting element moving to-and-fro within the stationary application part, which cuts off tissue sucked into the opening of the application part in co-action with the edge of the opening. As a drive for the cutting element moving to-and-fro in the application part, an electric motor is provided, which is arranged in the hand piece.

A disadvantage of this instrument is that the removed tissue, first of all, is sucked into the opening and, subsequently, is cut off, so that it cannot be prevented that also vessels are sucked into the opening and cut, which may result in considerable bleedings.

A further disadvantage of such an instrument is that the instrument itself has a high weight due to the motor integrated in the hand piece, which results in a quick fatigue of the user's hand. Furthermore, a movement transforming element is necessary in order to transform the rotation movement of the motor into an axial movement of the cutting element. This movement transforming element is also relatively large and heavy, and losses occur in the transformation from the rotation movement into the axial movement of the cutting element.

For the disintegration of soft tissue, purely mechanical instruments are also known, which are configured in the shape of cannulas, these being connected to a common syringe. By moving to-and-fro the cannula by hand, fatty tissue can be separated and sucked off by means of the syringe.

The disadvantage of these instruments is that by the mechanical movement transmitted by hand and the large lengths of stroke resulting therefrom of the to-and-fro movement, not only fatty tissue, but also blood vessels and other tissue may be removed, which may result in inner injuries and inflammations.

Further, from U.S. Pat. No. 4,886,491, a method for tissue removal with an ultrasound instrument is known, in which an ultrasound suction cannula is entered into the body in the area of the soft tissue or the fatty tissue. The cannula is excited to high frequency oscillations with low amplitude by means of ultrasound, whereby a local mechanical tissue disintegration, but also additional frictional heat is generated. The disintegrated fatty tissue is then sucked off via the cannula.

The disadvantage of ultrasound supported tissue removal is that operations of longer duration, as it is the case particularly in the abdominal area, which may last up to four hours, cause a significant heating of the ultrasound hand piece, which cannot be prevented even by additional irrigation. Moreover, the ultrasound hand pieces with the piezo-oscillators are relatively large and heavy. This is a problem in particular for fat removal in the face area. Apart from that, the piezo-elements are to be run with relatively high voltages, which causes additional insulation problems and safety problems. Also, the tissue removal speed or the disintegration speed is not satisfying.

On the other hand, it could be envisaged to use the instrument of WO 99/09897 used in pneumatic lithotripsy, which is used for fragmentation of hard concrements, like e.g. body stones, in modified form also for removal of tissue, in particular soft tissue and fatty tissue. In this known instrument for pneumatic lithotripsy, a bolt movable in a probe is axially moved to-and-fro by means of compressed-air impulses, wherein the probe impulse transmitted by the bolt fragmentizes the concrement to be dissolved.

Another lithotripter of that kind is known from DE 44 05 656 A1, in which the probe transmitting the shock waves runs in a stationary guide tube, which has a take-in and/or suction conduit for the stones that were smashed by the probe.

The disadvantage of such pneumatic lithotripsy instruments is the low repeat frequency of the movement of the probe, which is less than 20 Hz, and the relatively large hand piece. The low repeat frequency of the probe movement is due to the fact that pressure impulses have to be generated, and that the bolt has to be moved back into its initial position after each shot. Apart from that, besides the hand piece and a compressed-air supply, an additional device for the generation of pressure impulses is necessary. Such a pneumatic lithotripsy instrument, which is optimized for the fragmentation of concrements due to the very high probe speed and the very strong probe impulse, is extremely expensive for the removal of tissue or bone cement.

The instrument known from DE 34 39 434 A1 mentioned at the outset has as application part a probe, a cannula or a needle, in the distal part of which there is a linear motor having a piston, which is moved to-and-fro by a pressure of a fluid, in order to generate oscillations up to approximately 20 kHz, to reach different biological effects in different parts of the body, even deep in the inner part of the body. This known instrument is not adapted for the removal of soft tissue and fatty tissue due to the configuration of the application part, which is formed by the piston itself.

The invention has, thus, the object to provide an instrument of the type mentioned at the outset, by which tissue, in particular soft tissue and fatty tissue, can be removed without the danger of bleedings and inner injuries, as well as bone cement and the like.

SUMMARY OF THE INVENTION

This object is achieved by a medical instrument for treating, in particular a medical instrument for treating, in particular for removing tissue, bone cement or the like in the human or animal body, comprising:

a hand piece having a distal end;

an application part arranged at said distal end of said hand piece, said application part being axially movable to-and-fro relative to said hand piece, said application part having at least in a region of a distal end of said application part a conduit, which has, in a distal region of said conduit, at least a suction and/or irrigation aperture; and a drive mechanism for said application part, said drive mechanism being provided in said hand piece, said drive mechanism transferring a pressure being continuously present in said hand piece into said to-and-fro movement of said application part.

In the instrument according to the invention, the application part itself is, thus, axially movable to-and-fro relative to the hand piece, whereby the tissue to be removed is gently loosened by the application part. In particular fat particles may be released from the tissue compound and sucked off through the configuration according to the invention as hollow probe, and/or an irrigation liquid may be fed into the area to be treated in order to facilitate sucking off tissue or bone cement.

In comparison to the known instruments in which the tissue to be cut off is sucked through an opening into the application part and is cut off by a cutting element, the danger of cutting off or cutting blood vessels and, thus, of bleedings is avoided.

Just the combination of the application part being moved to-and-fro by the existing pressure and its simultaneous configuration as a hollow probe result in a construction that is simple in design and in a particular suitability of the instrument for the removal of soft tissue and fatty tissue.

While the known shaver instruments solely cut actively the tissue to be removed, the instrument of the invention allows tissue compounds to be mechanically dissolved and/or to be disintegrated. By making use of a continuously present pressure as drive mechanism for the application part, the pressure being transformed into a to-and-fro movement of the application part, in comparison to the instruments known from the pneumatic lithotripsy, the advantage is created that the repeat frequency of the to-and-fro movement can be increased considerably. Repeat frequencies of more than 50 Hz can be reached. In comparison to purely mechanical instruments, which are moved to-and-fro by hand, and for which the stroke of movement is large and not exactly controllable, the stroke of movement of the application part can be, due to the drive mechanism, limited to approximately 0.1 mm to 5 mm or to 10 mm, depending on the application. The instrument of the invention is not only suited for the removal of tissue or bone cement, but can also be used advantageously for stimulation of tissue areas by transmission of kinetic energy into the tissue area to be treated for the therapy of inflammations or articulation diseases, nervous inflammations or for the stimulation of the blood circulation.

Due to the simple and cost-effective construction, the instrument can also be manufactured as one-way instrument, so that cleaning and sterilization can be omitted.

In a preferred embodiment, the pressure is created by compressed air and the drive mechanism is configured in the manner of a pneumatic-mechanical oscillating circuit, which has as active elements the pneumatic pressure and at least one energy storage element, preferably a spring.

By this configuration, a cost-effective drive mechanism that is simple in construction for the application part is created, which combines the continuously present pressure with an energy storing element, in particular a spring, to a pneumatic-mechanical oscillating circuit.

In another preferred embodiment, the compressed air is generated in an external compressed-air source and is supplied to the hand piece via a line.

In this method, it is advantageous that the hand piece itself can be configured in a slender fashion and low in weight because the compressed-air source needs not to be located in the hand piece. A compressed-air bottle, a local or a central compressor system (hospital internal compressed-air supply) may be used as compressed-air source.

In a further preferred embodiment, the drive mechanism has a pressure chamber arranged in the hand piece, which has at least a proximal air inlet opening and, arranged on the distal side thereof, at least a lateral air outlet opening is arranged, and in the pressure chamber there is a piston connected to the application part, which is biased by the energy storing element in the direction against the pressure.

By this measure, a pneumatic-mechanical oscillating circuit is created that is particularly simple in design and easy to be maintained, wherein the oscillation of the drive mechanism and, thus, the to-and-fro movement of the application part is caused by the combination of the piston with the at least one lateral air outlet opening. The continuously present pressure moves the piston into the distal direction, thus tensing the spring, wherein the piston in its movement into the distal direction clears the at least one air outlet opening, out of which the compressed air can escape, whereby the pressure in the pressure chamber is reduced and the spring moves back the piston after the air outlet, after which the pressure in the pressure chamber is increased again, so that, altogether, a periodic movement of the application part is caused.

In another preferred embodiment, the pressure in the pressure chamber is adjustable via an adjustable pressure reducing valve.

It is advantageous herewith that the continuous pressure present in the pressure chamber can be adjusted in relation to the energy storing element and, thus, the movement speed of the application part and the length of stroke of the movement of the application part. Alternatively to a pressure reducing valve, the acting cross section of the air inlet opening, e.g. in form of an iris diaphragm, can also be variable in order to control the filling procedure of the pressure chamber.

In preferred embodiments, the pressure reducing valve in the hand piece is either arranged on the proximal side of the pressure chamber, or it is arranged in an external device between the compressed-air source and the hand piece.

Furthermore, it is also preferred if the pressure reducing valve is arranged directly on or in the compressed-air source.

In that way, the adjustment of the pressure present in the pressure chamber can be adjusted directly at the compressed-air source.

It is further preferred if the at least one suction and irrigation aperture is arranged laterally on the application part.

Due to the lateral arrangement of the opening, a danger of injury is avoided by the edges of the opening in the axial to-and-fro movement, while this is not guaranteed for an opening at the distal end of the application part.

In another preferred embodiment, a distal point of the application part is closed and configured approximately in spherical cap shaped fashion.

While this configuration of the distal end is advantageously suited for the disintegration of soft tissue or fatty tissue, because a more gentle treatment of the tissue is guaranteed, it is also preferred according to another embodiment, if the application part has a distally open point, which forms the suction and irrigation aperture.

In this case, a gouge-like configuration is reached, by which bone cement in connection with the to-and-fro movement of the application part can be particularly efficiently removed. In this procedure, the edges of the distal open point can be additionally sharpened.

In further preferred embodiments, in the proximal region of the conduit, a connection piece for connecting a suction and/or irrigation line is arranged on the distal side of the hand piece, or the conduit extends until into the hand piece and opens into a connection piece at the proximal end of the hand piece for connecting a suction and/or irrigation line.

In the latter alternative, there is the advantage of a straight conduit for a better sucking off of removed tissue, and another advantage is a lesser disturbing influence of the user by any hoses in the region of the application part.

It is further preferred if the application part has at least one conduit for insufflation of a fluid into the treatment area.

In this embodiment, the disintegration of the tissue can be advantageously accelerated by insufflating a suitable fluid, whereby the duration of the treatment can be reduced in particular for fat removal operations.

It is further preferred if the at least one suction and/or irrigation aperture is configured as a blade on its edge.

By this measure, the tissue removal can be improved by the combination of mechanical disintegration and additional cutting effect of the edge of the irrigation opening when moving to-and-fro the application part, wherein, as distinguished from the known instruments, in which the tissue is solely sucked into the opening and cut off by means of a cutting element, in this method, a danger of blood vessel injuries is reduced.

In another preferred embodiment, the length of stroke and/or the frequency of the to-and-fro movement of the application part is adjustable.

It is advantageous herewith that the instrument according to the invention can be adapted to the respective application with respect to the stroke of movement or to the movement amplitude. The adaptability is preferably within a range of 0.1 mm to 5 mm or larger, e.g. 10 mm.

To this end, in another preferred embodiment, the effective cross section of the at least one air outlet opening can be reduced and enlarged.

By enlarging the air outlet opening, the pressure in the pressure chamber is reduced faster, when the piston clears the air outlet opening, whereby the movement amplitude of the piston is reduced, because the force stored in the energy storage, e.g. in the form of a spring, as counter force to the present pressure, exceeds the pressure already after shorter time and, thus, shorter movement way due to the faster pressure reduction and moves back the piston into the proximal direction. By reducing the air outlet opening, the stroke of movement of the piston is correspondingly enlarged until its return.

In particular, by an axial change of the effective cross section of the at least one air opening, essentially a change of the length of stroke of the application part can be reached, while a circumferential change of the effective cross section can result in a faster air outlet and, thus, in another frequency of the to-and-fro movement.

The stroke of movement and/or the frequency of the piston can, in that way, be adjusted by controlling the air outlet.

It is further preferred in this procedure, if around the pressure chamber an axially and/or circumferentially movable sleeve is arranged for continuous covering or exposing the at least one air outlet opening.

In this way, in a simple design and in an easy to handle manner, a regulating element for reducing and/or enlarging the air outlet opening and, thus, for reducing and/or enlarging the stroke of movement of the piston is created.

In order to effect also an additional electrically caused tissue disintegration, it is also preferred if the application part has at least one electrically insulated electrode, which is supplied with a high frequency voltage. In the case of only one electrode, the disintegration can be done in monopolar manner, in the case of two electrodes, the disintegration can be done in bipolar manner.

The tissue disintegration can also be advantageously improved, if additionally a generator element generating ultrasound can be coupled onto the application part.

In another preferred embodiment, the application part can be detached from the hand piece.

In that way, the instrument can easier and more thoroughly be cleaned due to the fact that it can be disassembled into hand piece and application part.

An even further improvement of the instrument according to the invention is reached in a preferred embodiment by arranging an endoscopic system in the application part, which transmits images and/or light, whereby the application of the instrument is endoscopically visualized in the treatment area and, thus, can be controlled.

Further advantages can be taken from the following description and the attached drawings.

It is to be understood that the features mentioned above and those yet to be explained below can be used not only in the respective combinations indicated, but also in other combinations or in isolation, without leaving the scope of the present invention.

BRIEF DESCRIPTION OF THE DRAWINGS

An embodiment of the invention is shown in the drawings and will be explained in more detail in the description below. In the drawings:

FIG. 1 shows a medical instrument for treating, in particular for removing tissue, bone cement or the like in the human or animal body in a longitudinal sectional view in a first instantaneous operating position of the application part;

FIG. 2 shows the instrument in FIG. 1 in a second instantaneous operating position of the application part;

DETAILED DESCRIPTION OF PREFERRED EMBODIMENTS

Figure 3:
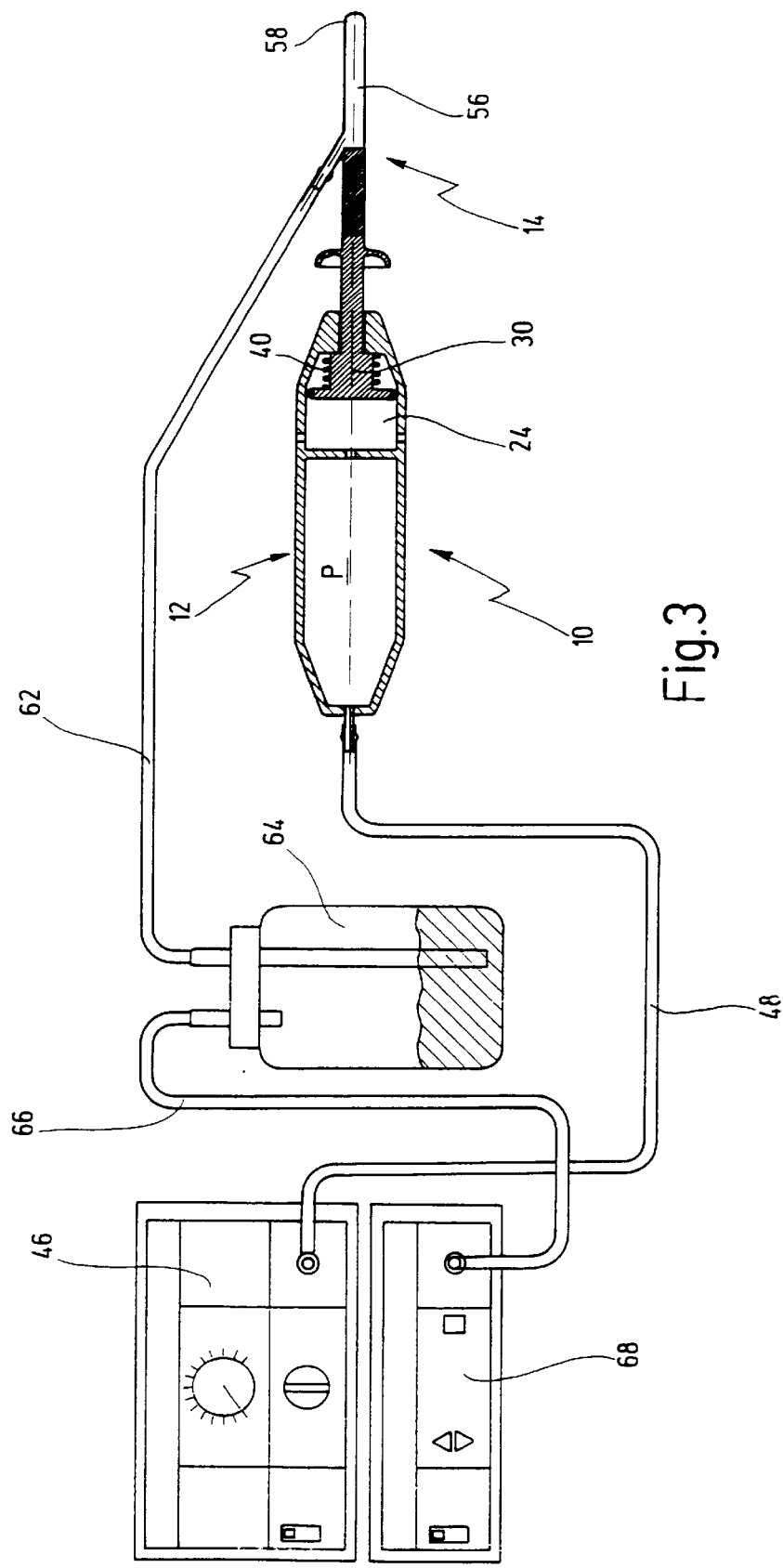
FIG. 3 shows a total device for treating, in particular for removing tissue, bone cement or the like in the human or animal body with the instrument in FIG. 1 and 2.

In FIGS. 1 through 3, a medical instrument is depicted provided with the general reference numeral 10, by means of which tissue in the human or animal body can be treated. Instrument 10 serves particularly for removing tissue, in particular soft or fatty tissue, or for removing bone cement, by means of which an endoprothesis is implanted in a bone of the skeleton. Instrument 10 can also be used for the stimulation of tissue areas by transmission of kinetic energy into the tissue area to be treated for therapy of inflammations, articulation diseases, nervous inflammations or for the stimulation of the blood circulation.

Instrument 10 has a hand piece 12 and an application part 14 that is arranged at the distal end of hand piece 12.

Application part 14 is axially movable to-and-fro relative to hand piece 12, as is indicated with a double arrow 16.

In order to move application part 14 to-and-fro according to double arrow 16, a drive mechanism 18 is provided in hand piece 12 for application part 14, which transforms a continuously present pressure into the to-and-fro movement of application part 14, as is described in the following.

Hand piece 12 has a housing 20, which divides hand piece 12 into a proximal chamber 22, in which the pressure designated as p is present continuously, and into a distal pressure chamber 24.

The proximal chamber and pressure chamber 24 are separated by a partition wall 26, wherein in partition wall 26 an air inlet opening 28 is recessed. Air inlet opening 28 is arranged centrally in partition wall 26 and passes through partition wall 26.

In pressure chamber 24, a piston 30 is arranged, which is connected to application part 14 via an axial extension piece 32, extension piece 32 projecting into housing 20 of hand piece 12 seen from application part 14.

Piston 30 has a seal 34 in form of an O-ring, whereby pressure chamber 24 is divided into a proximal part 36 of chamber 24 and into a distal part 38 of chamber 24, wherein proximal part 36 of chamber 24 is pressure-tight sealed by seal 34 against distal part 38 of chamber 24. In other words, only proximal part 36 of chamber 24 is supplied with continuously present pressure p via air inlet opening 28.

Piston 30 is further biased into the proximal direction with an energy storing element 40 in form of a compression spring arranged in pressure chamber 24. Energy storing element 40 acts, thus, against continuously existing pressure p.

In the part of housing 20 surrounding pressure chamber 24, two lateral air outlet openings 42 and 44 are recessed, which extend only over a partial circumference of pressure chamber 24 in circumferential direction.

Pressure p is generated by compressed air, which, according to FIG. 3, is continuously generated in an external compressed-air source 46 and which is supplied into proximal chamber 22 of hand piece 12 via a line 48 in order to generate continuous pressure p there.

With the afore-described elements of pressure p generated by compressed air and energy storing element 40 in form of the spring, a pneumatic-mechanical oscillating circuit is formed, which leads to the periodical to-and-fro movement of application part 14, as is described in the following.

Starting from the position of the piston being axially arranged in pressure chamber 24 depicted in FIG. 1, in which seal 34 is located on the proximal side of air outlet openings 42 and 44, the continuous present pressure in proximal chamber 22 and through air inlet opening 28 also in proximal part 36 of pressure chamber 24 causes piston 30 to be pushed into distal direction against the force of energy storing element 40. As soon as piston 30 is moved so far in distal direction by the ventilation of proximal part 36 of pressure chamber 24 that seal 34 is located on the distal side of air outlet openings 42 and 44, proximal part 36 of pressure chamber 24 is deaerated by escaping of the compressed air from air outlet openings 42 and 44, as is indicated with arrows 50 and 52. In that way, the pressure is reduced in proximal part 36 of pressure chamber 24, whereby stretched energy storing element 40 moves back piston 30 from the position shown in FIG. 2 into the position shown in FIG. 1, from which the process is repeated. This results in the periodical to-and-fro movement of application part 14 according to double arrow 16. The positions of piston 30 in FIG. 1 and FIG. 2 are to be understood as instantaneous exposures of the periodical movement.

The stroke of movement of application part 14 is determined by continuous present pressure p, the spring constant of energy storing element 40 and the effective cross sections and position of air outlet openings 42 and 44 and of air inlet opening 28.

For the adjustment of continuously present pressure p, an adjustable pressure reducing valve not shown is provided, which can be arranged e.g. in the hand piece, namely on the proximal side of proximal chamber 22, or which can be arranged in an external device not shown between compressed-air source 46 and hand piece 12 or it may be arranged on or in compressed-air source 46 itself and can be adjusted via a corresponding actuation element. The ventilation process of pressure chamber 24 with air can also be controllable by the fact that the air inlet opening is reducible or enlargeable in its cross section, for example, the air inlet opening can be configured in form of an iris diaphragm.

In FIG. 1, a correspondingly sealed sleeve 54 is further schematically depicted, which is arranged at housing 20 in an axially and/or circumferentially movable way, by which the length of stroke and the frequency of the to-and-fro movement of application part 14 are also adjustable, as sleeve 54 is provided with suitable openings 53 and 55, which, depending on their axial or circumferential position, are not, partly or completely in alignment with air outlet openings 42 and 44, whereby the effective cross sections of air outlet openings 42 and 44 are reduced or enlarged, so that the compressed air escapes faster or slower or sooner or later from air outlet openings 42 and 44. If sleeve 54 clears, for example, a larger effective cross section of air outlet openings 42 or 44, the compressed air can escape faster from these air outlet openings 42 or 44, whereby pressure p is reduced faster in proximal part 36 of pressure chamber 24, whereby the distal dead point of the movement of piston 30 is displaced into the proximal direction. If the effective cross section of air outlet openings 42 and 44 is reduced, the distal dead point of the movement of piston 30 is further displaced into the distal direction.

The length of stroke of the to-and-fro movement of application part 14 can be varied, in this way, in a range of 0.1 mm to 5 mm or up to 10 mm.

The repetition frequency of the periodical to-and-fro movement, which can be reached with this pneumatic-mechanical oscillating circuit, is more than 50 Hz.

Figure 4:
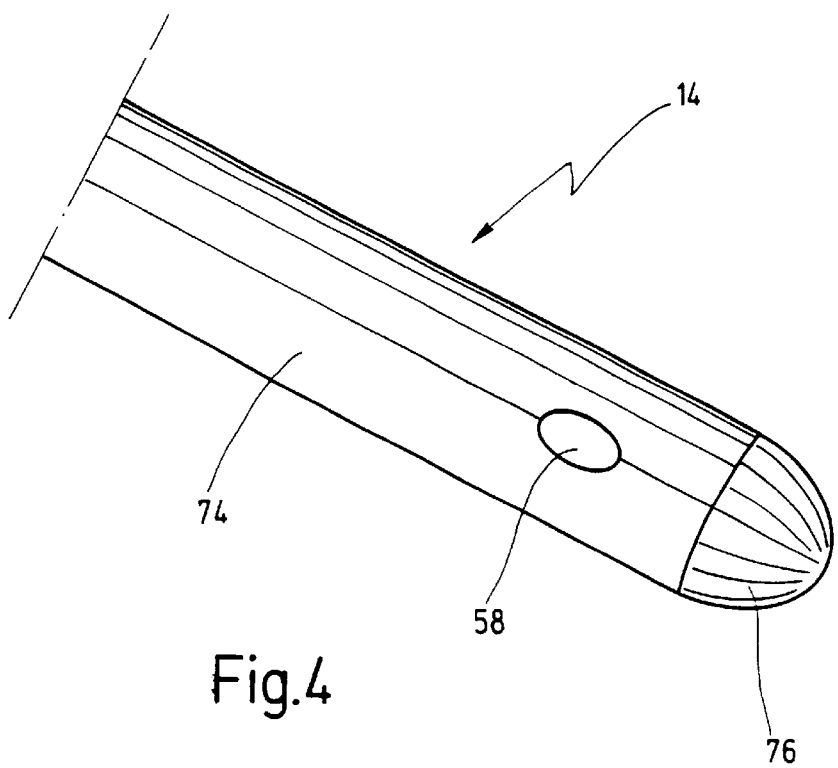
FIG. 4 shows the distal end of the application part of the instrument in an enlarged perspective view.

In the following, the configuration of application part 14 is described in detail, the distal end of which is in enlarged manner shown in FIG. 4.

Application part 14 has in the region of its distal end a conduit 56, so that application part 14 is configured as a hollow probe in the region of its distal end. Conduit 56 has a laterally arranged suction and irrigation aperture 58. According to FIG. 4, application part 14 has a cylindrical tube 74 with a point 76, which is configured approximately in spherical cap shaped fashion. In special applications, like e.g. in cataract surgery or for the removal of the lens in the eye, also a frontal opening may be advantageous.

In the proximal region of conduit 56, a connection piece 60 is further arranged on the distal side of hand piece 12, for connecting a suction and irrigation line 62, as is shown in FIG. 3. In the embodiment shown, suction and irrigation line 62 is merely configured as a suction line, which is conducted in a vacuum container 64. Tissue that was disintegrated and removed by application part 14 can be sucked into vacuum container 64 via suction line 62. In order to generate vacuum that is necessary for suction in vacuum container 64, vacuum container 64 is connected to a suction pump 68 via a line 66.

Conduit 56 itself in application part 14 or another conduit not shown in application part 14 may serve for insufflation of a fluid into the treatment area.

Moreover, the edge of lateral suction and irrigation aperture 58 can be configured as a cutting edge, in order to generate an additional mechanical cutting effect for the removal of tissue or for the disintegration of tissue, due to the to-and-fro movement of application part 14. Another configuration is to insert a kind of lattice in the opening, via same a multiple cutting or rasping is possible.

Application part 14 itself can be detached from hand piece 12, as application part 14 is connected to piston 30 via a releasable connection 70, e.g. in form of a screw connection, more precisely, with axial extension piece 32 of piston 30.

At axial extension piece 32 of piston 30, further, an air repeller 72 is provided to prevent compressed and not sterile air escaping from air outlet openings 42 or 44 from being blown into the treatment area.

Instrument 10 is particularly suited within the scope of minimal-invasive surgery for the disintegrating removal of fatty tissue, wherein application part 14 is introduced by a small incision. After switching on compressed-air source 46, application part 14 carries out a periodical to-and-fro movement as described before, which results in destruction of cell structures in a mechanical way and, thus, in disintegration of fatty tissue. If suction pump 68 is switched on, the disintegrated fatty tissue is, at the same time, sucked into conduit 56 through suction and/or irrigation opening 58 and drained off into vacuum container 64 via connection piece 60 and line 62.

In another embodiment not shown, the application part can be surrounded by an outer sleeve at least at its proximal side, e.g. in form of an insert aid, so that the puncture area is not directly exposed to the moving application part.

In further improvements of application part 14, which are not depicted, same can have at least one electrically insulated electrode, which is supplied with a high frequency voltage, so that, in addition to the mechanical tissue removal due to the periodical to-and-fro movement of application part 14, the disintegrating effect can be reinforced by high frequency current.

Moreover, an ultrasound generating element may be coupled to application part 14, so that in addition to the to-and-fro movement of application part 14, a high frequent vibration may be superimposed to same, whereby the disintegration is also reinforced.

In order to allow sight control of the treatment in the scope of the minimal-invasive surgery, an endoscopic system is arranged in application part 14, which transmits images and/or light.

It is also possible to make conduit 56 of application part 14 project into hand piece 12 until the proximal end thereof and to arrange connection piece 60, then, onto the proximal end of hand piece 12.

Figure 5:
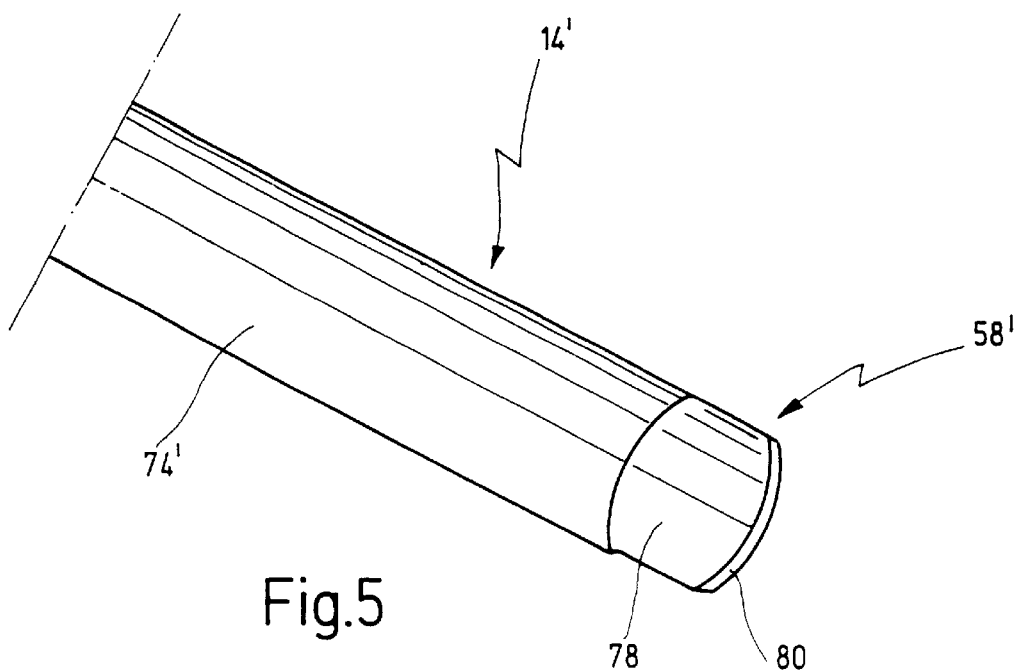
FIG. 5 shows an alternative embodiment for the distal end of the application part.

In FIG. 5, in another embodiment, a distal end of an application part 14' is shown, which can be connected to instrument 10 instead of application part 14. Application part 14' has a cylindrical tube 74', the distal end of which has an open point 78 serving as suction and irrigation opening 58'. Point 78 has a sharpened edge.

This embodiment of application part 14' in form of a gouge is particularly adapted for the removal of bone cement.

What is claimed is:

1. A medical instrument for removing tissue, bone cement or organic or synthetic materials from a human or animal body, comprising:

a hand piece having a distal end;

an application part arranged at said distal end of said hand piece, said application part being axially movable to-and-fro relative to said hand piece, said application part having at least in a region of a distal end of said application part a conduit, which has, in a distal region of said conduit, at least one of a suction and an irrigation aperture;

a drive mechanism for said application part, said drive mechanism being provided in said hand piece, said drive mechanism transferring a pressure being continuously present in said hand piece into said to-and-fro movement of said application part; and a sleeve operable to control the configuration of an air outlet opening so as to adjust at least one of a length of stroke and a frequency of said to-and-fro movement of said application part.

2. The instrument of claim 1, wherein said pressure is created by compressed air and said drive mechanism is configured in the manner of a pneumatic-mechanical oscillating circuit, which has as active elements said pneumatic pressure and at least one energy storage element.

3. The instrument of claim 2, wherein said compressed air is generated in an external compressed-air source and is supplied to said hand piece via a line.

4. The instrument of claim 3, wherein said drive mechanism has a pressure chamber arranged in said hand piece, which has at least a proximal air inlet opening and, arranged on a distal side of said pressure chamber, at least a lateral air outlet opening, and wherein in said pressure chamber a piston connected to said application part is arranged, which is biased by said energy storing element in a direction against said pressure.

5. The instrument of claim 4, wherein said pressure in said pressure chamber is adjustable via an adjustable pressure reducing valve.

6. The instrument of claim 5, wherein said pressure reducing valve in said hand piece is arranged on a proximal side of said pressure chamber.

7. The instrument of claim 1, wherein said drive mechanism has a pressure chamber arranged in said hand piece, and wherein pressure in said pressure chamber is adjustable via an adjustable pressure reducing valve, and wherein said pressure reducing valve is arranged in an external device between said compressed-air source and said hand piece.

8. The instrument of claim 7, wherein said pressure reducing valve is arranged directly on or in said compressed-air source.

9. The instrument of claim 1, wherein said at least one of a suction and an irrigation aperture is arranged laterally on said application part.

10. The instrument of claim 1, wherein a distal point of said application part is closed and configured approximately in spherical cap shaped fashion.

11. The instrument of claim 1, wherein said application part has a distally open point, which forms said at least one of a suction and an irrigation aperture.

12. The instrument of claim 1, wherein in a proximal region of said conduit a connection piece for connecting at least one of a suction and an irrigation line is arranged on a distal side of said hand piece.

13. The instrument of claim 1, wherein said conduit extends until into said hand piece and opens into a connection piece as a proximal end of said hand piece for connecting at least one of a suction and an irrigation line.

14. The instrument of claim 1, wherein said application part has at least one conduit for insufflation of a fluid into an area of treatment.

15. The instrument of claim 1, wherein said at least one of a suction and an irrigation aperture has an edge configured as a blade.

16. The instrument of claim 1, wherein said drive mechanism has a pressure chamber arranged in said hand piece, which has at least a proximal air inlet opening and, arranged on a distal side of said pressure chamber, at least a lateral air outlet opening, and wherein in said pressure chamber a piston connected to said application part is arranged, which is biased by said energy storing element in a direction against said pressure and wherein an effective cross section of said at least one air outlet opening can be reduced and enlarged.

17. The instrument of claim 16, wherein around said pressure chamber a sleeve is arranged for continuous covering or exposing said at least one air outlet opening, which sleeve is axially movable.

18. The instrument of claim 16, wherein around said pressure chamber a sleeve is arranged for continuous covering or exposing said at least one air outlet opening, which sleeve is circumferentially movable.

19. The instrument of claim 1, wherein said application part has at least one electrically insulated electrode, which is supplied with a high frequency voltage.

20. The instrument of claim 1, wherein additionally a generator element generating ultrasound can be coupled onto said application part.

21. The instrument of claim 1, wherein said application part can be detached from said hand piece.

22. The instrument of claim 1, wherein in said application part an endoscopic system is arranged, which transmits at least one of images and light.

* * * * *